US00PP32758P2

(12) United States Plant Patent
Yanny

(10) Patent No.: US PP32,758 P2
(45) Date of Patent: Jan. 19, 2021

(54) ***CARPINUS* PLANT NAMED 'JN SELECT AA'**

(50) Latin Name: *Carpinus caroliniana*
Varietal Denomination: JN Select AA

(71) Applicant: Michael D. Yanny, Milwaukee, WI (US)

(72) Inventor: Michael D. Yanny, Milwaukee, WI (US)

(73) Assignee: JN PLANT SELECTIONS, LLC, Milwaukee, WI (US)

( * ) Notice: Subject to any disclaimer, the term of this patent is extended or adjusted under 35 U.S.C. 154(b) by 40 days.

(21) Appl. No.: 16/501,959

(22) Filed: Jul. 10, 2019

(51) Int. Cl.
*A01H 5/00* (2018.01)
*A01H 6/00* (2018.01)

(52) U.S. Cl.
USPC ..... Plt./216

(58) Field of Classification Search
USPC ..... Plt./216
CPC ... A01H 5/02; A01H 5/00; A01H 5/04; A01H 6/00
See application file for complete search history.

*Primary Examiner* — June Hwu
(74) *Attorney, Agent, or Firm* — Penny J. Aguirre

(57) ABSTRACT

A new cultivar of *Carpinus* plant named 'JN Select AA' that is characterized by its foliage that consistently turns pinkish red in color in the fall in southern Wisconsin, its rounded plant habit and dense branching, and its good cold hardiness in southern Wisconsin.

2 Drawing Sheets

Genus/species: *Carpinus caroliniana.*
Varietal denomination: 'JN Select AA'.

BACKGROUND OF THE INVENTION

The present invention relates to a new and distinct cultivar of *Carpinus caroliniana* and will be referred to hereafter by its cultivar name, 'JN Select AA'. 'JN Select AA' represents a new cultivar of American hornbeam, ironwood, or musclewood; a deciduous tree grown for landscape use.

The Inventor discovered the new cultivar in spring of 2007 as a chance seedling that was growing in a block of seedlings that had been planted with seed derived from open pollination of unnamed and unpatented plants of *Carpinus caroliniana* from the Inventor's breeding program in Menomonee Falls, Wis. in 2011. Both the female and male parent are unknown.

Asexual propagation of the new cultivar was first accomplished in July of 2009 by side-veneer grafting onto seedling *Carpinus caroliniana* understock by the Inventor in Menomonee Falls, Wis. Asexual propagation by side-veneer grafting and cleft grafting has determined that the characteristics of the new cultivar are stable and are reproduced true to type in successive generations.

SUMMARY OF THE INVENTION

The following traits have been repeatedly observed and represent the characteristics of the new *Carpinus*. These attributes in combination distinguish 'JN Select AA' as unique and distinct cultivar of *Carpinus*.

1. 'JN Select AA' exhibits foliage that consistently turns pinkish red in color in the fall in southern Wisconsin.
2. 'JN Select AA' exhibits a rounded plant habit and dense branching.
3. 'JN Select AA' exhibits good cold hardiness in southern Wisconsin.

Typical plants of *Carpinus caroliniana* differ from 'JN Select AA' in having a plant habit that is not as dense and less rounded and in having fall color that is less red in color. 'JN Select AA' can be most closely compared to the *Carpinus caroliniana* cultivars 'JFS-KW6' (not patented) and 'JN Select A' (U.S. Pat. No. 29,969). 'JFS-KW6' is similar to 'JN Select AA' in having reddish fall color in southern Wisconsin. 'JFS-KW6' differs from 'JN Select AA' in having orange-red fall foliage color that develops later in fall, having less cold hardiness and exhibiting a high degree of winter damage (twig die-back) in severe winters in southern Wisconsin, and in having a less dense growth habit. 'JN Select A' is similar to 'JN Select AA' in having reddish fall color and in having good cold hardiness. 'JN Select A' differs from 'JN Select AA' in having orange-red fall foliage color, less dense branching, a more vigorous growth habit, and in developing a rounded plant habit as an older plant.

BRIEF DESCRIPTION OF THE DRAWINGS

The accompanying photographs depict the unique characteristics of 'JN Select AA' as grown in a trial garden in Menomonee Falls, Wis. The photographs were taken of 9-year-old plants.

Figure 1:
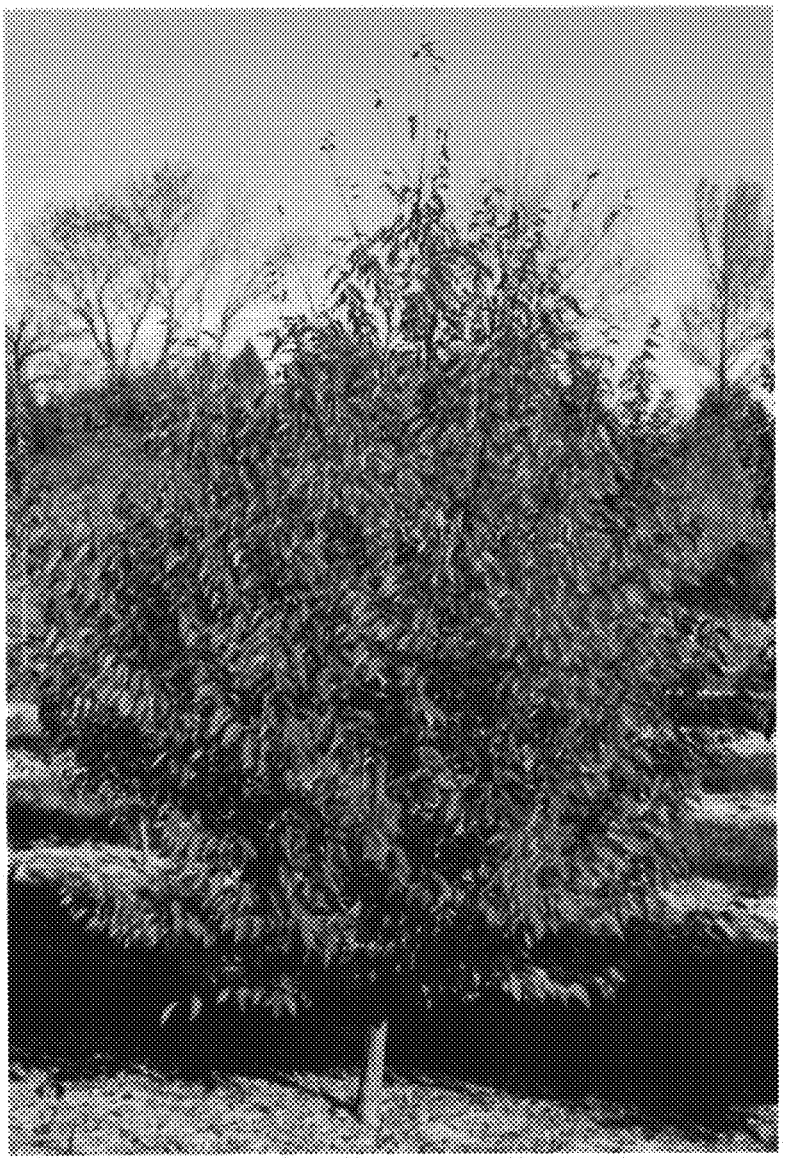
FIG. 1 provides a side view of the plant habit and fall foliage of 'JN Select AA'.
Figure 2:
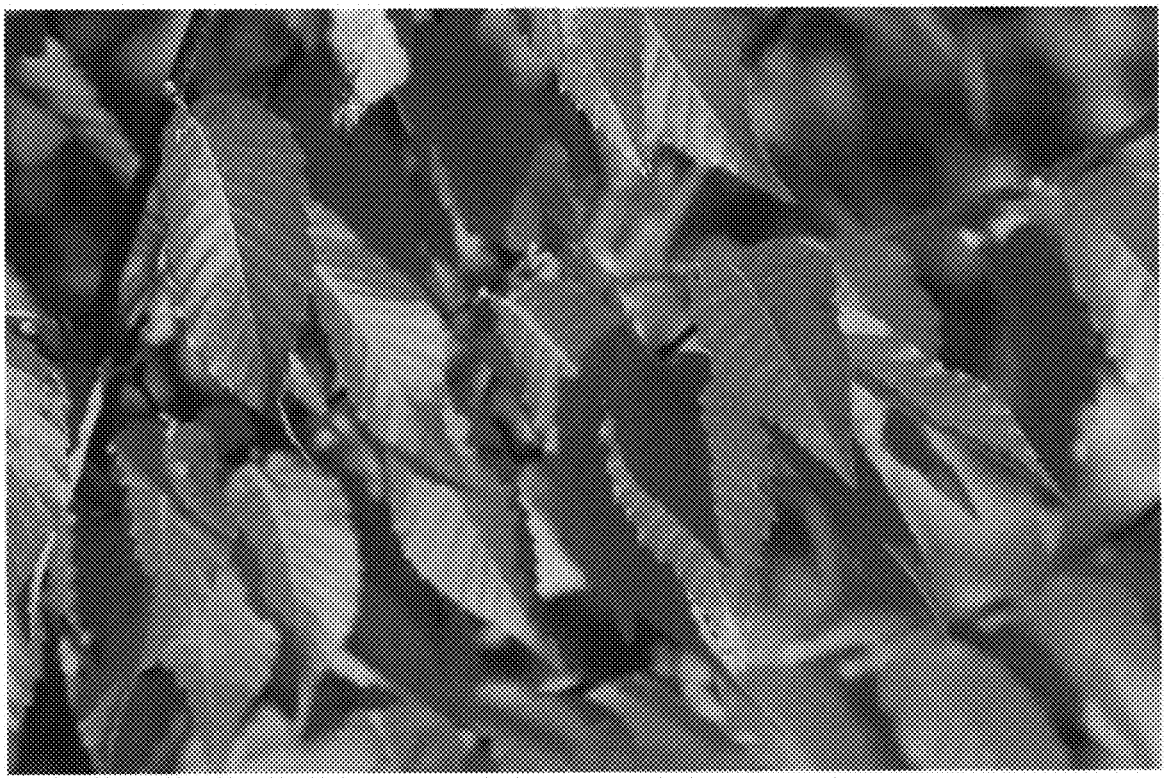

The photograph in FIG. 2 provides a close-up view of the fall foliage of 'JN Select AA'.

Figure 3:
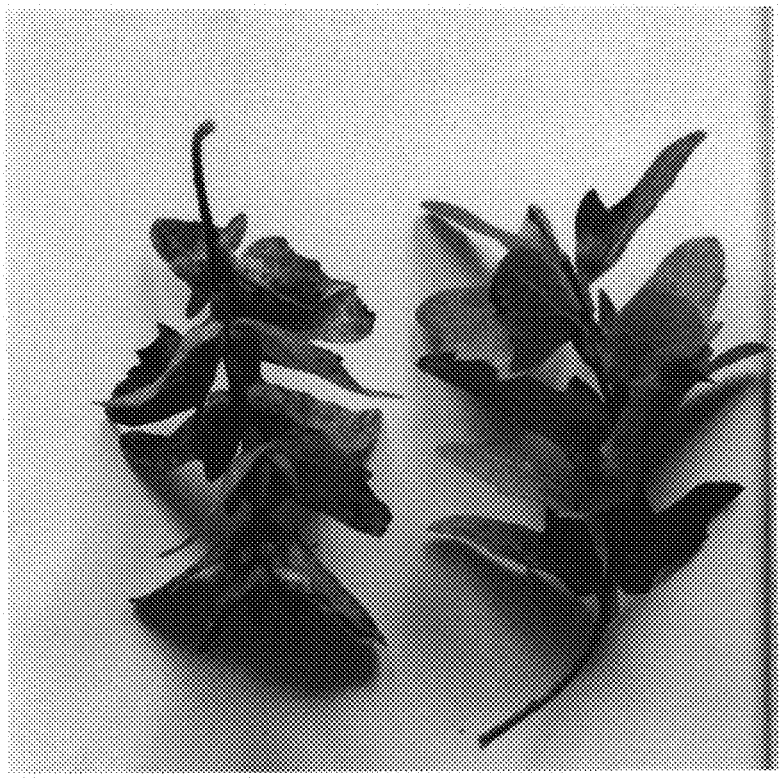

The photograph in FIG. 3 provides a close-up view of the fruit clusters and bracts of 'JN Select AA'.

The colors in the photographs are as close as possible with the digital photography and printing techniques utilized and the color codes in the detailed botanical description accurately describe the colors of the new *Carpinus*.

BOTANICAL DESCRIPTION OF THE PLANT

The following is a detailed description of 4-year-old plants as grown outdoors in 3-gallon containers in Menomonee Falls, Wis. Phenotypic differences may be observed with variations in environmental, climatic, and cultural conditions. The color determination is in accordance with The 2015 Colour Chart of The Royal Horticultural Society, London, England, except where general color terms of ordinary dictionary significance are used.

General description:

*Plant type.*—Deciduous tree.

*Plant habit.*—Upright and rounded.

*Height and spread.*—A mature plant in the landscape will reach 4 m in height and width.

*Hardiness.*—At least in U.S.D.A. Zone 4b to 7a with very little twig die-back observed due to winter in southern Wisconsin.

*Diseases and pests.*—No susceptibility or resistance to diseases or pests has been observed to date.

*Growth rate.*—Moderate.

*Propagation.*—Side-veneer grafting in mid to late July in a poly greenhouse under mist or cleft grafting in February with use of a hot callus pipe.

*Root development.*—A side veneer graft is produced in 6 to 8 weeks and 1.5 growing seasons are required to produce a whip 1.2 m in length in a 2-gallon container.

Branch description:

*Trunk size.*—An average of 1.7 cm cm in diameter measured 30 cm from soil line, 50 cm in length.

*Branch color.*—New growth (shoots) and second year growth 165A, mature wood and trunk; primarily 198A with some striations and underlying color of 165A.

*Branch shape.*—Rounded.

*Branch no. and size.*—Lateral branches (trunks divided into the 2 main branches); an average of 8 mm in diameter (mid stem) and 1.2 m in length, secondary branches; an average of 15 per lateral stem, up to 15 cm in length and 2.5 mm in diameter, small branchlets from tertiary branches; an average of 5 per branch 30 cm in length, up to 12 cm in length and 1.5 mm in width.

*Branch surface.*—New growth and one-year old twigs; glabrous, shiny and slightly pubescent, old growth twigs; glabrous, dull and lenticillate, trunk; dull and muscle-like, lenticels; moderate in number, lenticels on all branches and trunk are round in shape, 158A in color, up to 2 mm in diameter, an average of 10 lenticels per square cm.

*Branch angles.*—Alternately branched; lateral branch angles held about 20° to vertical and tertiary branches held at about a 45° angle.

*Leaf buds.*—An average of 5.5 mm in length and 2 mm in width, conical in shape, imbricate, 144A in color prior to bud break, glossy surface.

*Leaf bud break.*—Early May in Wisconsin.

*Stipules.*—None present.

Foliage description:

*Leaf shape.*—Oval-oblong.

*Leaf division.*—Simple.

*Leaf base.*—Rounded and slightly oblique.

*Leaf apex.*—Acute-slightly acuminate.

*Leaf venation.*—Pinnate, color; upper surface matches leaf color with very narrow midrib a color between 145B and 162C, lower surface 145C.

*Leaf margin.*—Biserrate.

*Leaf attachment.*—Petiolate.

*Leaf arrangement.*—Alternate.

*Leaf surface.*—Glabrous and smooth on upper and lower surfaces, lower surface has pubescence on veins.

*Leaf size.*—Up to 6 cm in length and 2.6 cm in width.

*Leaf internode length.*—An average of 1.9 cm.

*Leaf color.*—Emerging leaves; 172B quickly turning to 144A on upper and lower surface, mature; upper surface 146B and lower surface 146C, fall upper surface; a blend of 52A and 52B with veins and some suffusion of 25C, fall lower surface 163C and 39B.

*Petioles.*—An average of 1 cm in length and 1 mm in width, rounded in shape, 145C in color and suffused with 166B on upper surface, surface pubescent.

Flower description:

*Blooming period.*—Late April to early May in southern Wisconsin.

*Inflorescence.*—Monoecious, cylindrical male and female catkins.

*Catkins.*—Penduolous and cylindrical in shape, sparse on plant used for data collection; 4 male and 3 female, male; an average of 2.2 cm in length and 4 mm in diameter, scales; average of 18, broadly ovate in shape, an average 3 mm in length and width, apex; cuspidate, base; broadly cuneate, a blend of 145B and 144C in color with tip 175A on both surfaces, surfaces glabrous and pubescent on margins and apex, an average of 10 stamens per bract, stamens 145C in color, 0.5 mm in length on stout very short filament 145C in color, pollen low in quantity and 175A in color, female; an average of 1.1 cm in length and 3 mm in diameter, an average of 5 flowers with single bracts; elliptic in shape, 144A in color, 2 mm in length and 1.5 mm in width, and pubescent on both surfaces, 3 stigmas protruding about 2 mm and 60B in color.

*Flower fragrance.*—None.

*Flower lastingness.*—Female and male catkins present in spring for about 8 days, male not persistent.

*Peduncles* (*Rachis*).—Female; an average of 9 mm in length and 0.7 mm in diameter, male; 2.2 cm in length and 0.7 mm in diameter, both male and female: 144A in color, pubescent surface, moderately strong.

*Pedicels.*—None, sessile.

*Fruit and seed.*—Ribbed nutlet borne at the base of 3-lobed bracts and arranged in spike-like clusters, nutlet; average of 8 per cluster, an average of 4.5 mm in length and 3.5 mm in width, a blend of 147A and 146A in color, ovate in shape, seed; 1 per nutlet, 1 mm in length and 1.5 mm in width, 165A in color, fruit clusters; an average of 5 cm in length and 3.5 cm in width, bracts; tri-lobed, apex acute, margins serrate, base rounded, an average of 2 cm in length and 1.2 cm in width, glabrous on both surfaces, 144A in color when first developing and maturing to a blend of 146A, 178A and 178C when mature.

It is claimed:

1. A new and distinct cultivar of *Carpinus* plant named 'JN Select AA' substantially as herein illustrated and described.

* * * * *